United States Patent
Keyser et al.

(10) Patent No.: US 12,178,789 B2
(45) Date of Patent: Dec. 31, 2024

(54) STRESS TEST AND TREATMENT OF CHRONIC KIDNEY DISEASE

(71) Applicant: Renibus Therapeutics, Inc., Southlake, TX (US)

(72) Inventors: Donald Jeffrey Keyser, Southlake, TX (US); Alvaro F. Guillem, Lantana, TX (US); Bhupinder Singh, Phoenix, AZ (US); Richard A. Zager, Seattle, WA (US)

(73) Assignee: Renibus Therapeutics, Inc., Southlake, TX (US)

( * ) Notice: Subject to any disclaimer, the term of this patent is extended or adjusted under 35 U.S.C. 154(b) by 0 days.

(21) Appl. No.: 18/530,782

(22) Filed: Dec. 6, 2023

(65) Prior Publication Data

US 2024/0108589 A1 Apr. 4, 2024

Related U.S. Application Data

(62) Division of application No. 17/210,205, filed on Mar. 23, 2021, now Pat. No. 11,883,371.

(60) Provisional application No. 62/993,446, filed on Mar. 23, 2020.

(51) Int. Cl.
    *A61K 31/12*     (2006.01)
    *G01N 33/68*     (2006.01)

(52) U.S. Cl.
    CPC .......... *A61K 31/12* (2013.01); *G01N 33/6893* (2013.01); *G01N 2800/7009* (2013.01)

(58) Field of Classification Search
    CPC .................................................. A61K 31/12
    See application file for complete search history.

(56) References Cited

U.S. PATENT DOCUMENTS

| | | |
|---|---|---|
| 11,435,364 B2 | 9/2022 | Zager et al. |
| 11,883,371 B2 * | 1/2024 | Keyser ................... A61P 43/00 |
| 2005/0244983 A1 | 11/2005 | Ching |
| 2016/0058713 A1 | 3/2016 | Singh |
| 2020/0057076 A1 | 2/2020 | Zager et al. |

OTHER PUBLICATIONS

Search Report received in International Application No. PCT/US21/23747 dated Jul. 9, 2021, 3 pages.
Johnson et al., "Mechanisms and consequences of oxidant-induced renal preconditioning: an Nrf2-dependent, P21-independent, anti-senescence pathway," Nephrol Dial Transplant (2018) 33: Mar. 7, 2018, 15 pages.
Johnson et al., "Tin protoporphyrin activates the oxidant-dependent NRF2-cytoprotective pathway and mitigates acute kidney injury," The Fred Hutchinson Cancer Center Research Center, May 12, 2017, 18 pages.
Lau et al., "Dietary tetrahydrocurcumin reduces renal fibrosis and cardiac hypertrophy in 5 / 6 nephrectomized rats," Pharmacol Res Perspect, Nov. 27, 2017, 8 pages.
Search Report received in European Application No. 21776202.0-1112 dated Mar. 6, 2024, 11 pages.
Zager et al., "A Pharmacologic "Stress Test" for Assessing Select Antioxidant Defenses in Patients with CKD," Amican Society of Nephrology, vol. 15, May 2020, 10 pages.

* cited by examiner

*Primary Examiner* — Golam M Shameem
(74) *Attorney, Agent, or Firm* — CM Law; Jeff B. Vockrodt

(57) ABSTRACT

The present invention involves a novel method for treatment of chronic kidney disease comprising administering a compound that induces a stress protein response in a patient, and administering a potent antioxidant if the patent's response is below a predefined level. It also involves a quantitative measure for determining a patient's antioxidant reserve capacity.

7 Claims, 7 Drawing Sheets

STRESS TEST AND TREATMENT OF CHRONIC KIDNEY DISEASE

CROSS-REFERENCE TO RELATED APPLICATIONS

This application claims the benefit of U.S. Provisional Application No. 62/993,446, filed on Mar. 23, 2020, which application is hereby incorporated herein by reference.

BACKGROUND OF THE INVENTION

Oxidative stress is a hallmark and mediator of chronic kidney disease (CKD). Diminished anti-oxidant defenses are thought to be partly responsible. However, there is currently no way to prospectively assess anti-oxidant defenses in humans. Therefore a need exists for a quantitative measure of a patient's anti-oxidant defenses as well as methods of therapeutic treatments that take into account the patient's level of anti-oxidant response.

SUMMARY OF THE INVENTION

The present invention relates to a method for treating a patient comprising: (a) administering a compound to the patient, the compound being a transient oxidant stress inducer; (b) measuring the response of the patient to the compound, wherein the response comprises increased level of expression of one or more anti-oxidant proteins; and (c) administering a therapy to the patient if the level of expression of the one or more anti-oxidant proteins is above a predefined level. In one aspect, the patient may be suffering from chronic kidney disease. The compound may be a protoporphyrin, such as tin protoporphyrin, and the anti-oxidant proteins comprise one or more of HO-1, ferritin, p21, or NQ01. The therapy may include administering an antioxidant, such as tetrahydrocurcumin.

In one aspect, the method is conducted such that the level of expression of the one or more anti-oxidant proteins is measured before step (a), and the level of expression of the one or more anti-oxidant proteins measured in step (b) is compared to the level of expression measured before step (a).

In another aspect the present invention relates to a method comprising: (a) administering a compound to a patient, whereby the compound stimulates production of one or more antioxidant proteins in the patient; (b) obtaining one or more body fluid samples from a patient; and (c) measuring the level of the one or more anti-oxidant proteins produced in the patient. The compound may be a transient oxidant stress inducer, including a protoporphyrin or mesoporphyrin, such as tin protoporphyrin. The anti-oxidant may comprise one or more of HO-1, ferritin, p21, or NQ01. In another aspect, the level of production of the one or more anti-oxidant proteins is measured before step (a), and the level of expression of the one or more anti-oxidant proteins measured in step (c) is compared to the level of expression measured before step (a). The measured level of antioxidant proteins provides a quantitative measure of the anti-oxidant reserves of the patient.

DETAILED DESCRIPTION OF THE INVENTION

Figure 1:
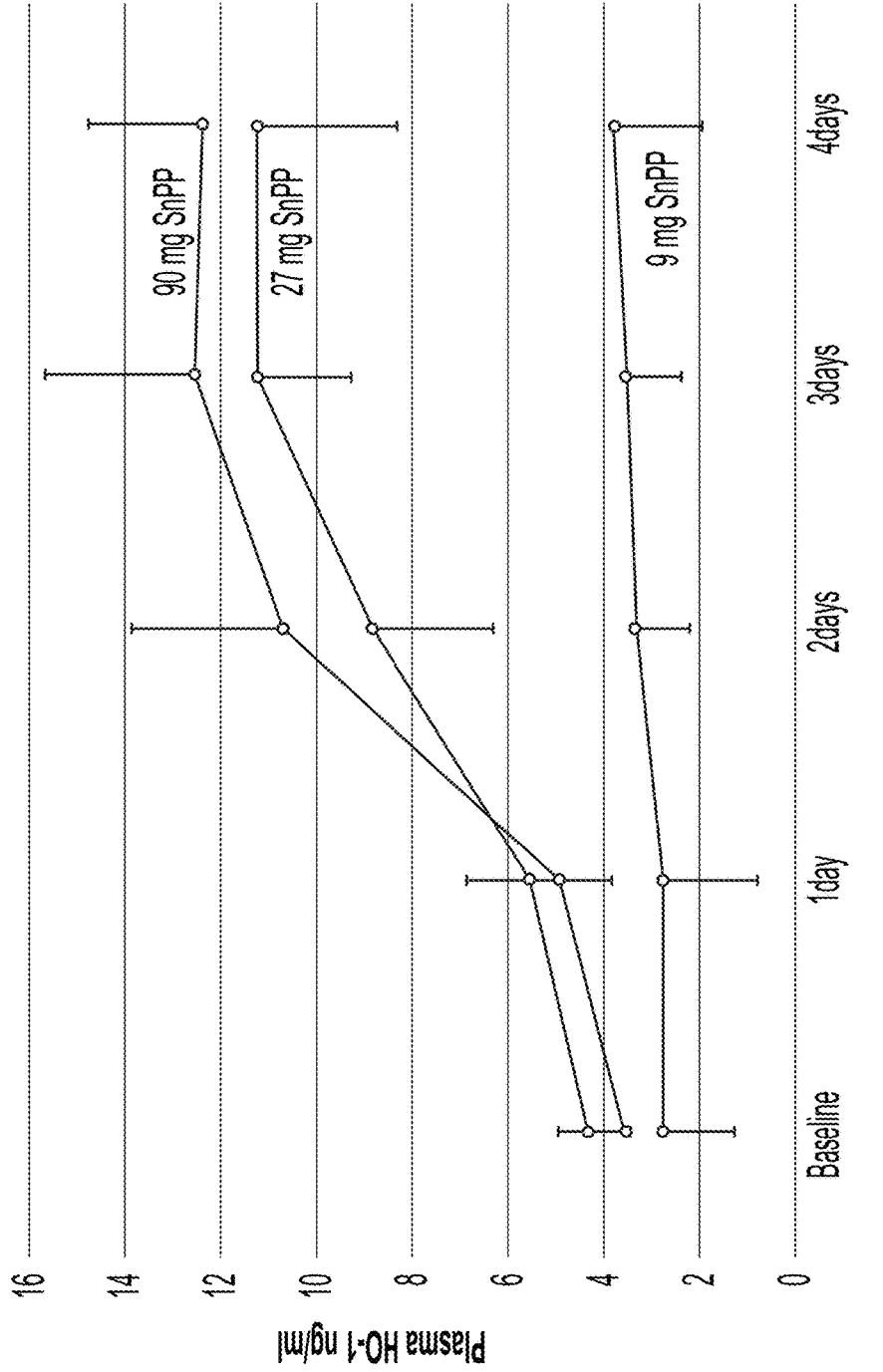
FIG. 1 shows plasma HO-1 levels rise in a dose dependent fashion following SnPP injection in healthy volunteers.

The present inventors have determined that SnPP can variably increase stress proteins in humans and thus, serve as a pharmacologic "stress test" for gauging their gene responsiveness and hence, anti-oxidant reserves. The stress test can be part of a method for treating chronic kidney disease by administering potent antioxidants to a patient for whom the test shows a lack of anti-oxidant reserves. The test can also be used to independently assess a patient's level of anti-oxidant reserves in order to further guide the patent's course of treatment.

In one respect, the invention involves a method of treating patients that includes steps of:
  (a) administering a compound to the patient, the compound being a transient oxidant stress inducer;
  (b) measuring the response of the patient to the compound, wherein the response comprises increased level of expression of one or more anti-oxidant proteins; and
  (c) administering a therapy to the patient if the level of expression of the one or more anti-oxidant proteins is above a predefined level.

The compound is preferably a protoporphyrin or mesoporphyrin such as tin protoporphyrin. The compound may be a zinc, tin or cobalt protoporphyrin or mesoporphyrin. The compound must be capable of inducing production of stress proteins in humans in a dose dependent fashion. This allows for a quantitative measure of the patient's antioxidant reserve capacity. The anti-oxidant proteins include one or more of HO-1, ferritin, p21, or NQ01. In one aspect, the invention measures the patient's baseline level of these proteins before administering the compound. This allows a comparison of the level of increase in the proteins that is induced by administration of the compound.

The particular methods disclosed herein are useful for treatment of conditions associated with chronic kidney disease. Where a patient undergoing treatment for chronic kidney disease lacks anti-oxidant reserve capacity, the patient may benefit from administration of potent antioxidants, e.g. tetrahydrocurcumin (19,20) or Nrf2 activators, e.g., bardoxolone methyl.

Another aspect of the invention is a method that allows measurement of a patient's anti-oxidant capacity in a dose dependent manner. This method includes steps of:
  (a) administering a compound to a patient, whereby the compound stimulates production of one or more anti-oxidant proteins in the patient;
  (b) obtaining one or more body fluid samples from a patient; and
  (c) measuring the level of the one or more anti-oxidant proteins produced in the patient.

The compound is preferably a transient oxidant stress inducer, such as tin protoporphyrin, or another protoporphyrin or mesoporphyrin. The administration of the compound induces stress proteins, such as one or more of HO-1, ferritin, p21, or NQO1. The level of these proteins induced provides a quantitative measure of the patient's antioxidant reserve capacity. Those patients having a capacity below a predefined value are candidates for potent antioxidant therapies.

The plasma HO-1 levels rose in a dose dependent fashion following SnPP injection in healthy volunteers as shown in FIG. 1. Plasma HO-1 levels were measured at baseline and from 1-4 days following 9, 27, or 90 mg SnPP injection. Time and dose dependent increases were observed (mean values/95% confidence intervals depicted). Significant increases of HO-1 values over time were observed in each subject group (all p values<0.001 as determined by ANOVA/repeated measures; within group analyses).

Figure 2:
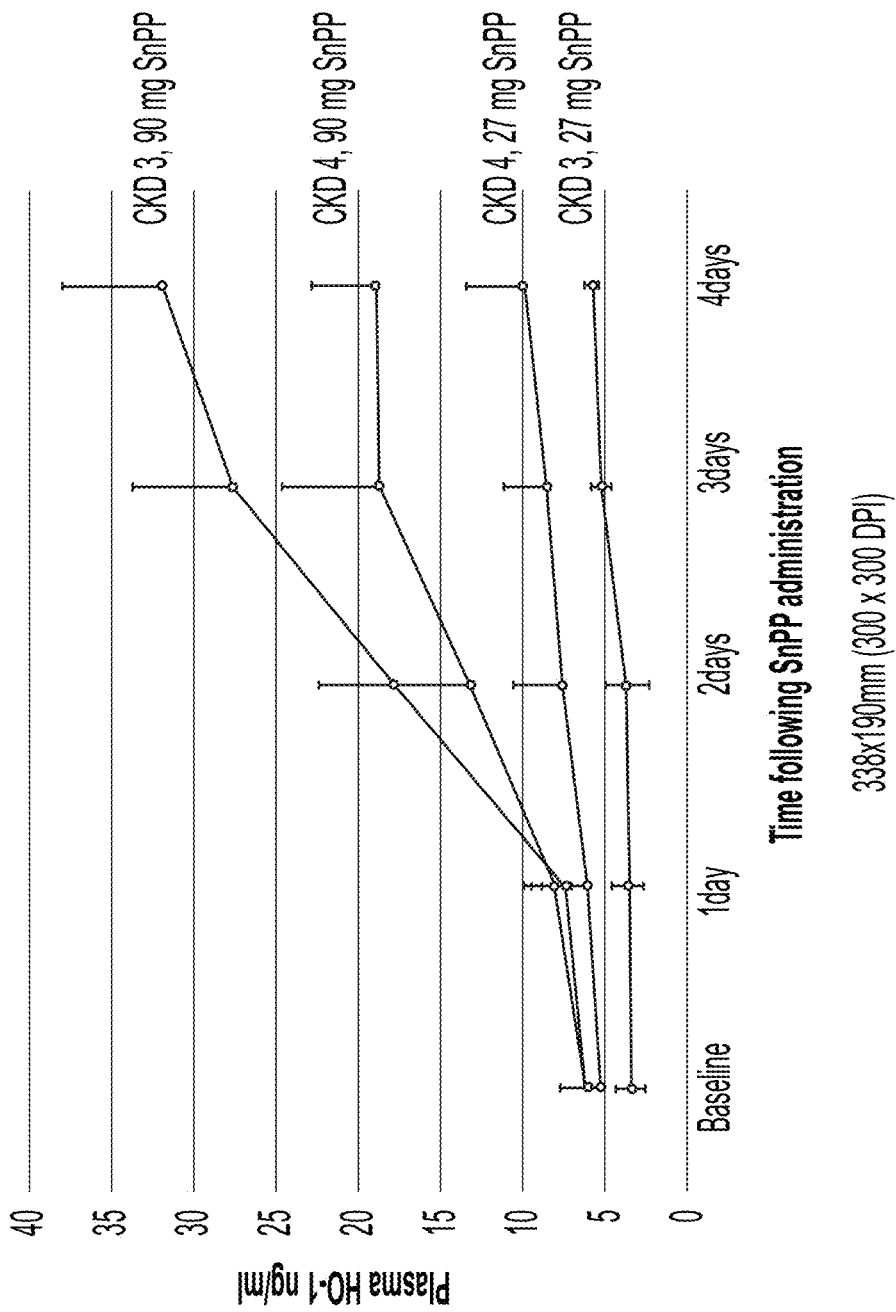
FIG. 2 shows plasma HO-1 levels rise following SnPP injection in stage 3 CKD (15-29 ml/min/1.73 m2) and stage 4 CKD (30-59 ml/min/1.73 m2) participants.

The plasma HO-1 levels rose following SnPP injection in stage 3 CKD (15-29 ml/min/1.73 m2) and stage 4 CKD (30-59 ml/min/1.73 m2) participants as shown in FIG. 2. Plasma HO-1 levels were measured at baseline and from 1-4 days following 27 mg or 90 mg SnPP injection. Time and dose dependent HO-1 increases were noted in both CKD3 and CKD4 groups. P<0.001, all in-group comparisons; ANOVA, repeated measures. The mean values/95% confidence intervals are depicted.

Figure 3:
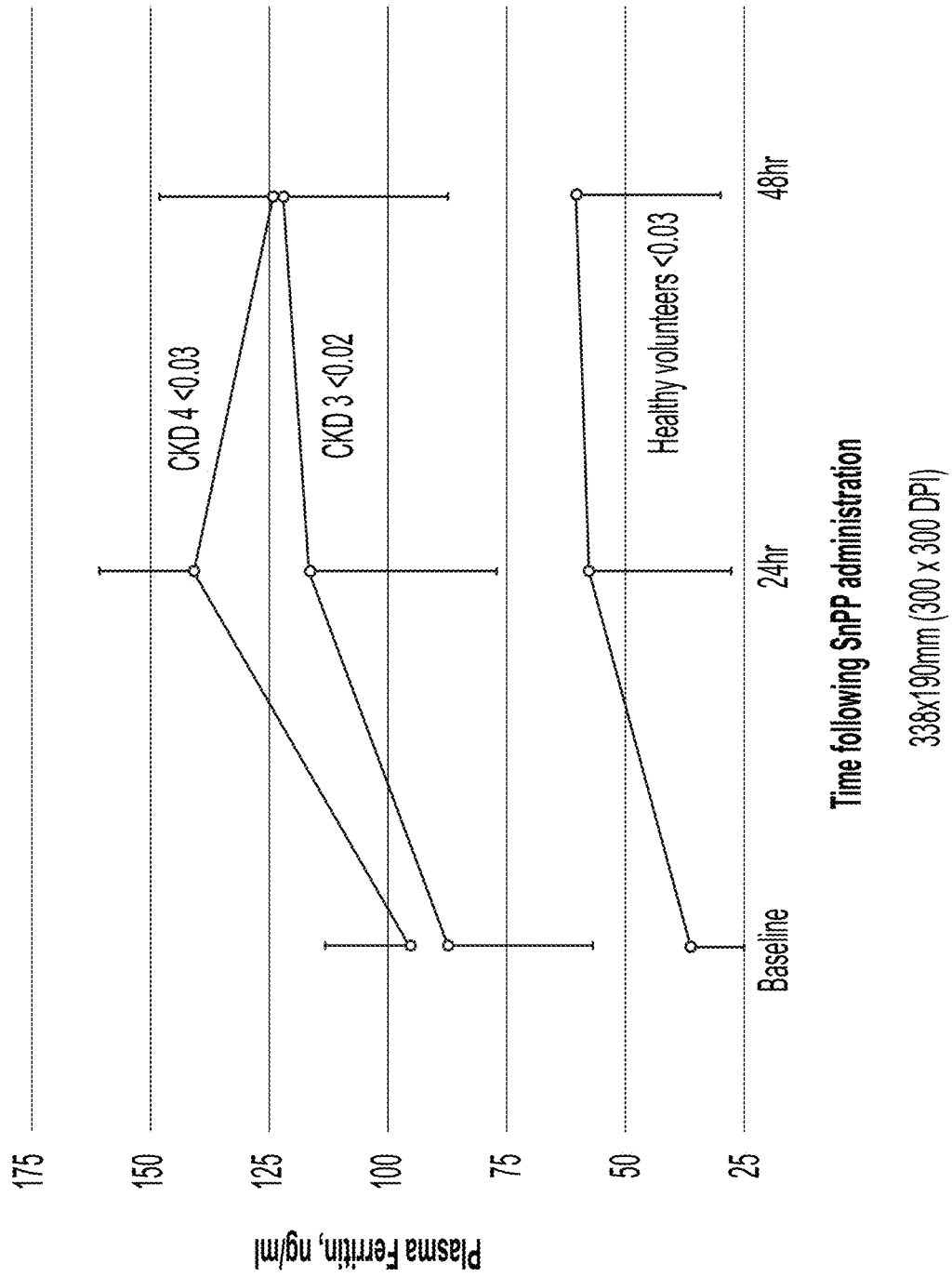
FIG. 3 shows plasma ferritin levels increase in response to SnPP injection.

The plasma ferritin levels increased in response to SnPP injection as shown in FIG. 3. Plasma ferritin levels were measured at baseline and 24+48 hrs following 90 mg SnPP injection in healthy volunteers and in CKD3/CKD4 participants. The CKD participants had significantly higher baseline ferritin levels, vs. the healthy volunteers (p<0.005 between group comparisons). All three groups manifested significant plasma ferritin increases following SnPP injection (p values by ANOVA, repeated measures; within group analyses). The increases over baseline values were comparable for the CKD and the healthy volunteer groups. Means/95% confidence intervals are depicted.

Figure 4:
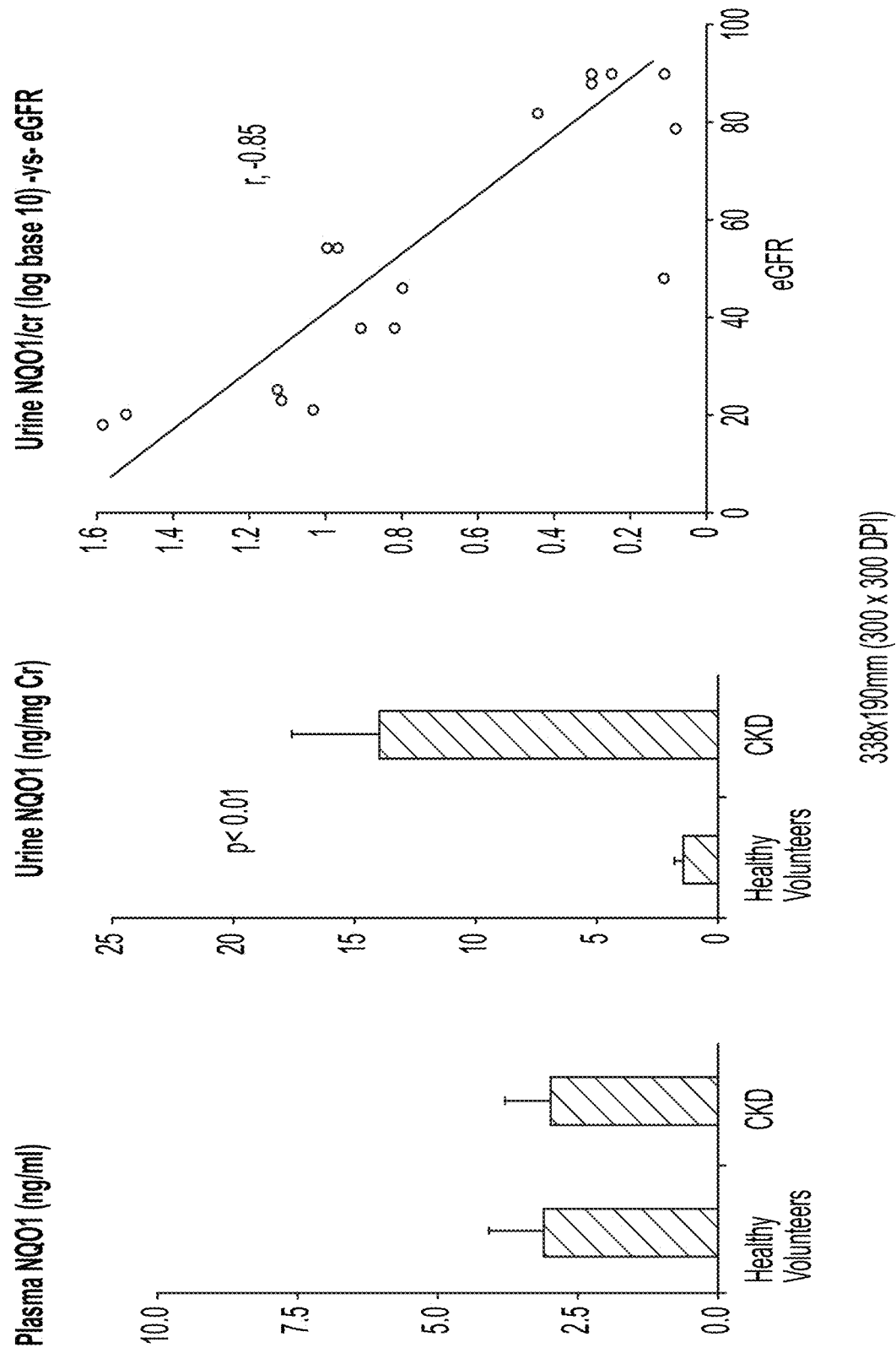
FIG. 4 shows baseline NQ01 levels in healthy volunteers and participants with CKD.

The baseline NQO1 levels in healthy volunteers and participants with CKD are shown in FIG. 4. The combined CKD cohorts and the healthy volunteers had virtually the same plasma NQO1 concentrations. However, CKD participants had markedly elevated urinary NQO1/creatinine levels (p<0.01; unpaired t test). When the urine NQO1/creatinine values were converted to log base 10, the individual values showed a strong inverse correlation with the corresponding baseline eGFRs for each subject (r, −0.85).

Figure 5:
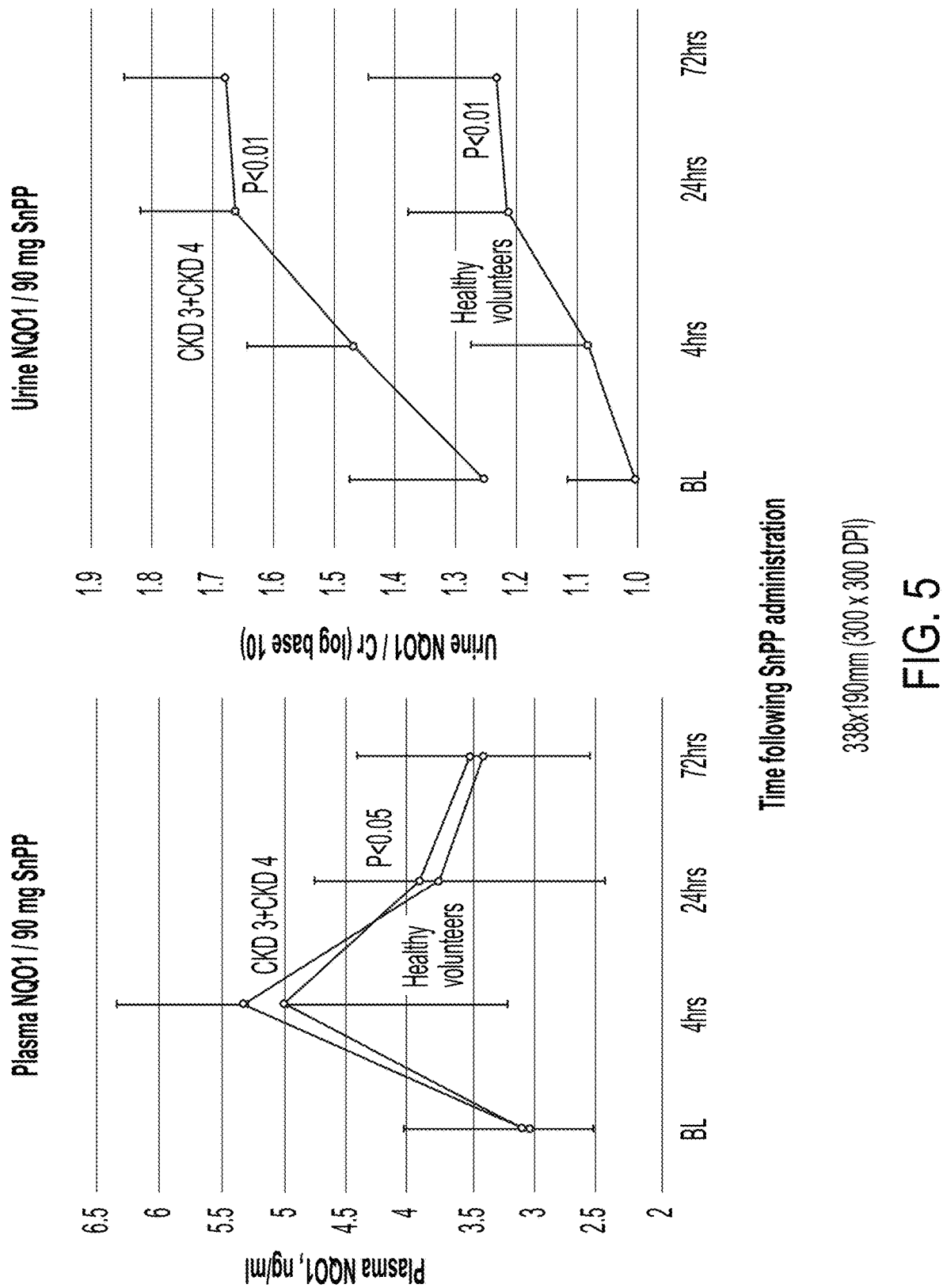
FIG. 5 shows plasma and urinary NQ01 responses to 90 mg SnPP infusion.

The plasma and urinary NQO1 responses to 90 mg SnPP infusion are shown in FIG. 5. The healthy volunteer and CKD participants showed acute, near identical increases in plasma NQO1 following 90 mg SnPP injection. Furthermore, the healthy volunteers and the combined CKD participants demonstrated significant, and progressive increases in urinary NQO1/creatinine levels over the 72 hr observation period. Though the healthy volunteers had lower baseline urinary NQO1 levels than the CKD participants, the slopes of the SnPP-induced urinary NQO1 increases over time were comparable for the healthy volunteer and CKD groups. Values are means/95% confidence intervals; urine values are after log base 10 conversion; statistics by ANOVA repeated measures, in-group comparisons.

Figure 6:
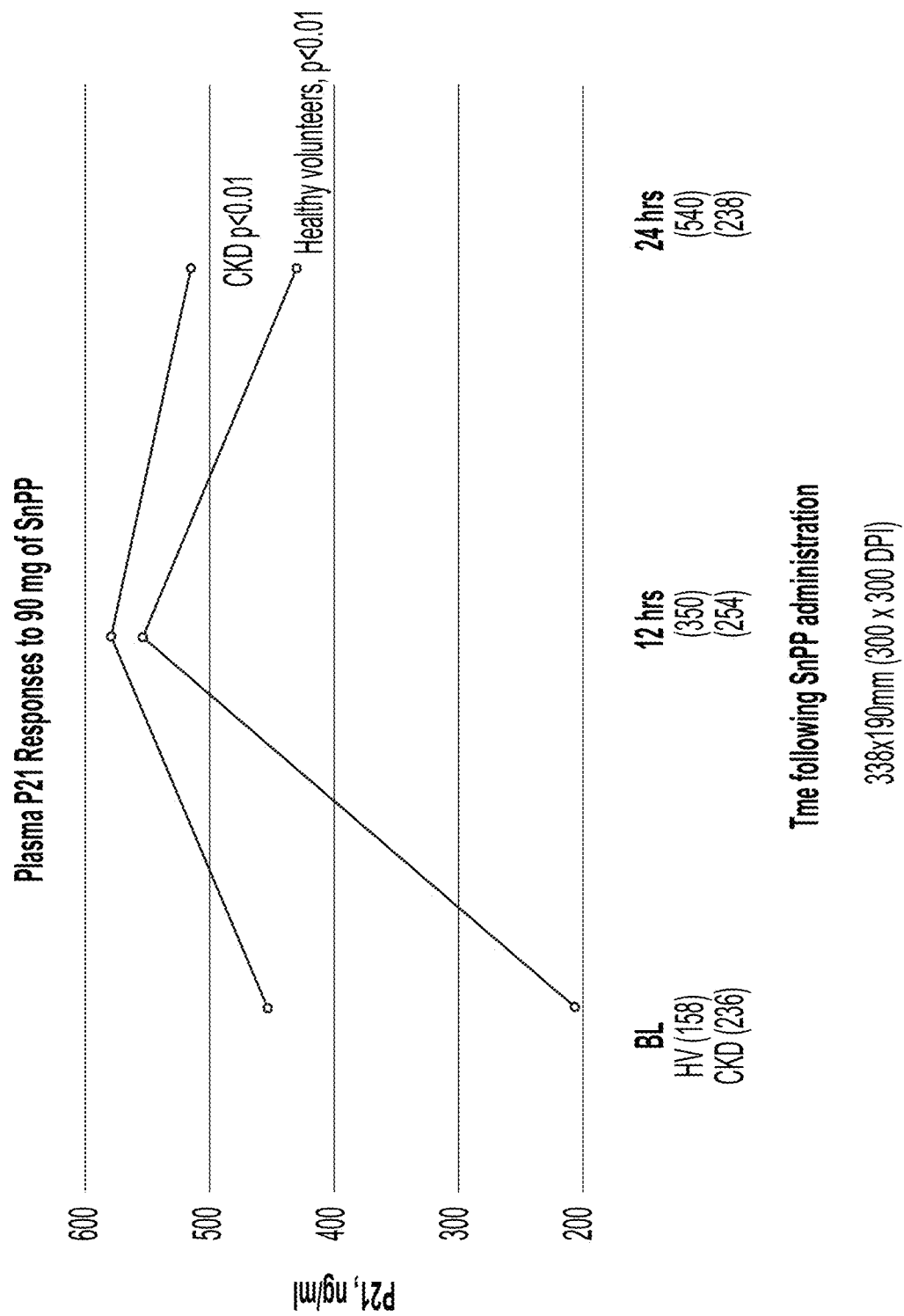
FIG. 6 shows plasma p21 concentrations at baseline and following SnPP injection.

The plasma p21 concentrations at baseline and following SnPP injection are shown in FIG. 6. There were marked variations in p21 values between participants, as reflected by large standard deviations (SDs: numbers in parentheses that appear at the bottom of the graph). (HVs=healthy volunteers; BL=baseline). However, despite this variation, the healthy volunteer and CKD participants demonstrated plasma p21 increases at 12 and 24 hrs post SnPP injection (CKD participants combined, p<0.01; healthy volunteers, p<0.01; ANOVA, repeated measures, in group comparisons). The fold increase over baseline values was significantly higher in the healthy volunteer vs. the CKD group (means of 2.65 vs 0.51, respectively; p<0.001; see text).

TABLE 1

Clinical characteristics of participants in three clinical trial arms evaluating intravenous tin protoporphyrin as a stress test of anti-oxidant capacity.

| Criterion | Healthy volunteers (N, 18) | CKD3 (N, 12) (30-59 ml/min/1.73 m$^2$) (N, 12) | CKD4 (15-29 l/min/1.73 m2) (N, 12) |
|---|---|---|---|
| Age | 43 (12) | 71 (8) | 71 (5) |
| Gender (M/F) | 72/28% | 34/66% | 67/33% |
| % White race | 50% | 75% | 75% |
| Weight (Kg) | 85 (15) | 85 (17) | 94 (20) |
| Diabetes | 0% | 42% | 66% |
| BP Systolic/Diastolic | 124/78 (18/9) | 139/76 (17/11) | 139/72 (24/9) |
| eGFR (ml/min/1.73 m$^2$) | 87 (4) | 42 (5) | 21 (4) |
| BUN (mg/dl) | 13 (3) | 30 (10) | 52 (20) |
| Creatinine (mg/dl) | 1.0 (0.2) | 1.5 (0.4) | 2.8 (0.5) |
| U albumin/creatinine (mg/gram) | <10 | 223 (480) | 519 (640) |
| Medications | | | |
| Statins | 0 | 50% | 67% |
| Antihypertensives | 0 | 67% | 83% |
| Diuretics | 0 | 35% | 8% |

Table 1 legend. Demographic and baseline clinical data for the three study cohorts. Mean values and standard deviations (numbers in parentheses) are presented. CKD 3, 15-29 ml/min/1.73 m$^2$; CKD4, 30-59 ml/min/1.73 m$^2$). For the three classes of medications, the percentages of participants within each group that were taking them are presented. BP, blood pressure; BUN, blood urea nitrogen.

TABLE 2

Estimated glomerular filtration rate after administration of 90 mg tin protoporphyrin.

| Group | Baseline | Day 2 post SnPP | Day 4 post SnPP |
|---|---|---|---|
| Healthy Volunteers | 84 ± 6 | 87 ± 5 | 88 ± 4 |
| CKD3 | 46 ± 6 | 50 ± 6 | 47 ± 6 |
| CKD4 | 20 ± 4 | 23 ± 5 | 22 ± 4 |

Table 2 legend. eGFRs are given as ml/min/1.73 m$^2$. CKD3 = eGFRs of 30-59 ml/min/m$^2$; CKD 4 = eGFRs of 5-29 ml/min/m$^2$. The values are given are means ± 1 SD. There were no significant eGFR changes from baseline in response to the highest test dose of tin protoporphyrin (90 mg).

TABLE 3

Urine biomarkers of kidney injury after administration of 90 mg tin protoporphyrin.

| Analyte; Participant subgroup | Baseline | Day 1 | Day 2 | Day 3 | Day 4 | P value |
|---|---|---|---|---|---|---|
| NAG; HVs (mU/mg Cr) | 2.0 ± 1.5 | 2.83 ± 1.167.5 | 3.16 ± 1.16 | 2.51 ± 0.64 | 2.66 ± 0.8 | 0.35 |
| NAG; CKD 3 | 4.4 ± 3.52 | 5.66 ± 3.44 | 8.2 ± 3.44 | 6.5 ± 1.7 | 5.9 ± 2.1 | 0.11 |
| NAG; CKD 4 | 9.0 ± 4.7 | 12.5 ± 11.34 | 10.6 ± 7.5 | 10.5 ± 5.6 | 6.2 ± 3.4 | 0.21 |
| NGAL; HVs (ng/mg Cr) | 14.3 ± 18.2 | 21.1 ± 28.7 | 14.8 ± 13.1 | 14.0 ± 8.7 | 10.2 ± 5.6 | 0.9 |
| NGAL; CKD 3 | 71.2 ± 64.1 | 46.5 ± 35.5 | 35.8 ± 23.2 | 49.8 ± 39.7 | 42.6 ± 51.7 | 0.41 |
| NGAL; CKD 4 | 46.5 ± 58.7 | 58.0 ± 79.1 | 64.8 ± 91.0 | 47.3 ± 60.2 | 48.0 ± 49.5 | 0.49 |
| Cystatin C; HVs (ng/mg Cr) | 30.0 ± 19.5 | 32.1 ± 15.1 | 34.8 ± 7.2 | 39.6 ± 9.4 | 40.4 ± 9.3 | 0.49 |
| Cystatin CKD 3 | 31.0 ± 7.7 | 26.8 ± 12.9 | 32.2 ± 9.8 | 34.0 ± 9.4 | 33.2 ± 33.2 | 0.35 |
| Cystatin CKD 4 | 298 ± 438 | 332 ± 519 | 638 ± 965 | 186 ± 213 | 207 ± 238 | 0.47 |
| KIM-1; HVs (ng/mg Cr) | 0.97 ± 0.5 | 0.7 ± 0.5 | 0.8 ± 0.7 | 0.7 ± 0.4 | 0.6 ± 0.4 | 0.5 |
| KIM-1; CKD 3 | 0.6 ± 0.2 | 0.8 ± 0.2 | 1.5 ± 0.6 | 1.4 ± 0.6 | 0.9 ± 0.2 | 0.08 |
| KIM-1 CKD 4 | 0.8 ± 0.5 | 0.8 ± 1.0 | 1.2 ± 1.0 | 1.2 ± 1.0 | 1.0 ± 0.8 | 0.11 |

Table 3 legend: The urinary biomarker values, as factored by urine creatinine (Cr). HVs = healthy volunteers; CKD 3 = CKD stage 3 (eGFRs 30-59 ml/min/1.73 m$^2$); CKD 4 = CKD stage 4 (eGFRs 15-29 ml/min/1.73 m$^2$). The eGFRs were assessed at baseline and days 1-4 post SnPP injection. No significant changes over time were observed for any of the analytes (see p values). KIM-1 = kidney injury molecule 1; NGAL = neutrophil gelatinase-associated lipocalin; NAG = n acetyl glucosaminidase. All values = means ± 1 SD. The p values are given for changes over time.

Figure 7:
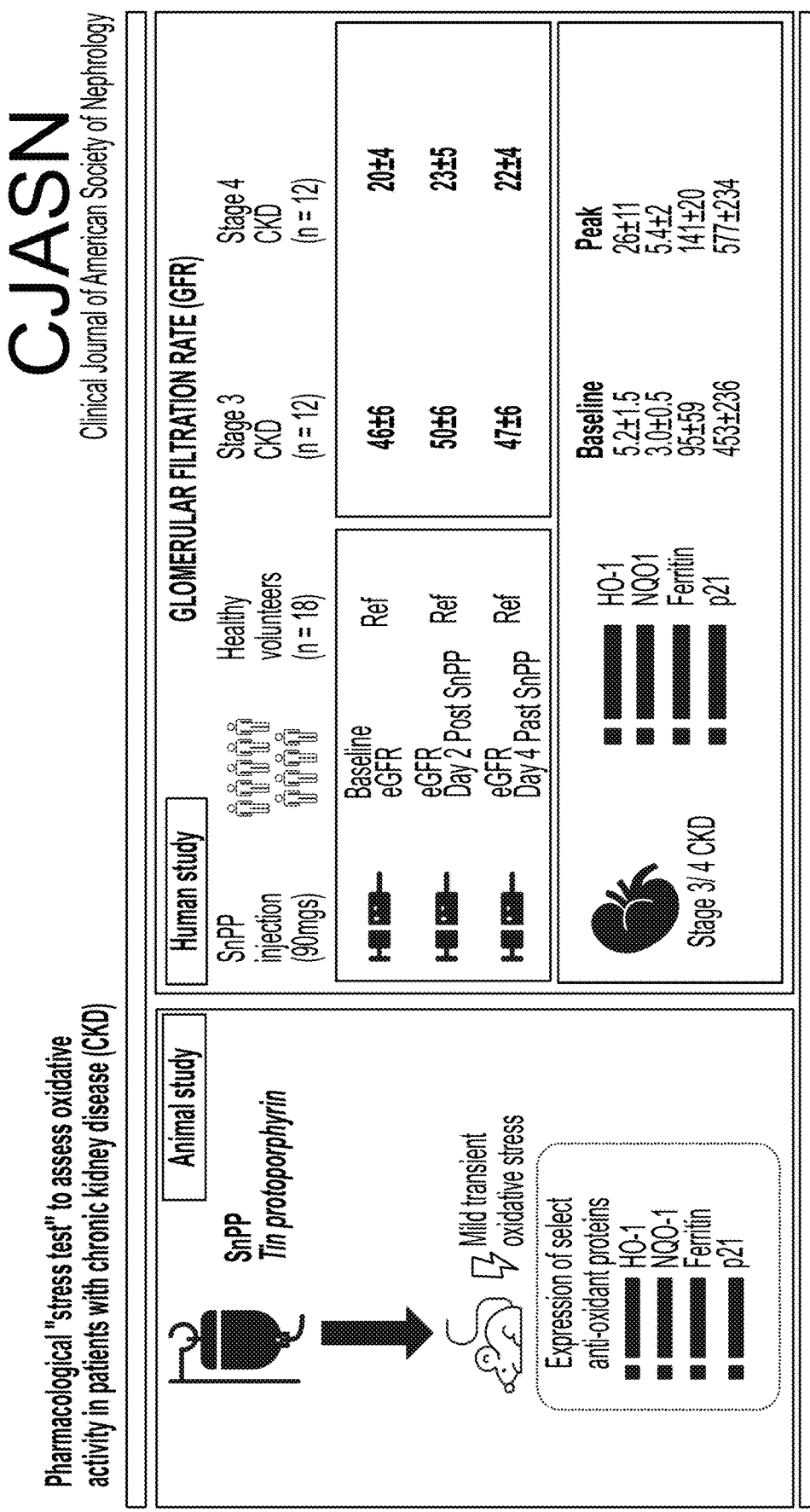
FIG. 7 shows baseline and peak plasma values of tested proteins demonstrating degrees of responsiveness to the highest tested dose of SnPP (90 mg).

Baseline and peak plasma values of tested proteins demonstrating degrees of responsiveness to the highest tested dose of SnPP (90 mg) are shown in FIG. 7. Baseline and maximal (peak) plasma anti-oxidant protein concentrations, as generated with the highest test dose of SnPP (90 mg). CKD=CKD 3 and CKD 4 groups combined. The data indicate the ability of SnPP to up-regulate HO-1, ferritin, NQO1 and p21 gene/protein expression. The values presented are means and 95% confidence intervals. Please see the figures for change of values over time and statistics by ANOVA for repeated measures. All peak values are significantly higher than baseline values, although the CKD group had a significantly blunted p21 response compared to the healthy volunteer group (see text). The timing of the peak values were 4 days, 12 hrs, 12 hrs and 4 hrs for HO-1, ferritin, p21, and NQ01, respectively.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A method comprising:
   (a) administering a compound to a patient, wherein the compound is a protoporphyrin or mesoporphyrin, which stimulates production of one or more antioxidant proteins in the patient;
   (b) obtaining one or more body fluid samples from a patient; and
   (c) measuring the level of the one or more anti-oxidant proteins produced in the patient.

2. The method of claim 1, wherein the compound is a transient oxidant stress inducer.

3. The method of claim 1, wherein compound is a metal protoporphyrin.

4. The method of claim 3, wherein the metal protoporphyrin is tin, cobalt, or zinc protoporphyrin.

5. The method of claim 1, wherein the anti-oxidant proteins comprise one or more of HO-1, ferritin, p21, or NQO1.

6. The method of claim 1, wherein the level of production of the one or more anti-oxidant proteins is measured before step (a), and the level of expression of the one or more anti-oxidant proteins measured in step (c) is compared to the level of expression measured before step (a).

7. The method of claim 1, wherein the measured level of antioxidant proteins provides a quantitative measure of the anti-oxidant reserves of the patient.

* * * * *